United States Patent [19]

Davis

[11] Patent Number: 4,921,477
[45] Date of Patent: May 1, 1990

[54] SURGICAL IRRIGATION AND ASPIRATION SYSTEM WITH DAMPENING DEVICE

[75] Inventor: Rickey P. Davis, Chino, Calif.

[73] Assignee: The Cooper Companies, Inc., Palo Alto, Calif.

[21] Appl. No.: 368,898

[22] Filed: Jun. 21, 1989

Related U.S. Application Data

[63] Continuation of Ser. No. 108,219, Oct. 14, 1987, abandoned.

[51] Int. Cl.⁵ ............................................. A61B 17/20
[52] U.S. Cl. ...................................... 604/22; 417/540; 604/119
[58] Field of Search ....................... 604/20, 22, 30, 31, 604/118, 119; 417/540

[56] References Cited

U.S. PATENT DOCUMENTS

| | | | |
|---|---|---|---|
| 2,448,118 | 8/1948 | Pelletteve | 417/540 |
| 2,474,512 | 6/1949 | Bechtold et al. | 417/540 |
| 3,589,363 | 6/1971 | Banko | 128/276 |
| 3,693,613 | 9/1972 | Kelman | 128/24 A |
| 3,902,495 | 9/1975 | Weiss et al. | 128/276 |
| 3,927,955 | 12/1975 | Spinosa et al. | 417/477 |
| 4,187,057 | 2/1980 | Xanthopoulos | 417/63 |
| 4,256,437 | 3/1981 | Brown | 417/45 |
| 4,493,706 | 1/1985 | Borsanyi et al. | 604/153 |
| 4,496,342 | 1/1985 | Banko | 604/27 |
| 4,604,034 | 8/1986 | Wheeldon et al. | 417/53 |

FOREIGN PATENT DOCUMENTS

86/07249 12/1986 PCT Int'l Appl. .
8606964 12/1986 PCT Int'l Appl. .

Primary Examiner—Jerome L. Kruter
Attorney, Agent, or Firm—Vorys, Sater, Seymour and Pease

[57] ABSTRACT

A surgical irrigation and aspiration system for aspirating fluid from a surgical site, such as the eye, including a surgical tool having irrigation and aspiration functions, and an irrigation fluid supply for providing irrigation fluid to the surgical tool. A peristaltic pump pumps aspiration fluid from the surgical site generally through and away from the surgical tool and through an aspiration flow line to a collection container. A dampening mechanism in the aspiration flow line before the pump dampens the oscillations of the aspiration fluid flow, caused by the inherent operation of the peristaltic pump, in the aspiration flow line, and thereby at the surgical site.

35 Claims, 3 Drawing Sheets

SURGICAL IRRIGATION AND ASPIRATION SYSTEM WITH DAMPENING DEVICE

This application is a continuation, of application Ser. No. 07/108,219, filed Oct. 14, 1987 now abandoned.

BACKGROUND OF THE INVENTION

The present invention relates to surgical irrigation and aspiration systems for aspirating fluid from a surgical site. It more particularly relates to aspiration tubing systems used in extracapsular cataract extraction, specifically phacoemulsification. The invention further relates to phacoemulsifier aspirators models which use peristaltic pumps to achieve their aspiration function.

Intraocular surgery, and the removal of cataracts in particular, has been greatly aided by the development of surgical instruments which include cutting or fragmenting means combined with means for irrigating the intraocular surgical site and aspirating therefrom the irrigating fluid together with any tissue fragments produced by the surgical procedure. A good example of this type of system is disclosed in U.S. Pat. No. 3,589,363, to Banko et al, whose contents are hereby incorporated by reference in their entirety. Other examples of fluid control systems are disclosed in Kelman, U.S. Pat. No. 3,693,613; Weiss et al, U.S. Pat. No. 3,902,495; and Banko, U.S. Pat. No. 4,496,342; each of whose entire contents are hereby incorporated.

Basically the surgical instruments disclosed therein and particularly in the '363 Banko patent comprise a handpiece which holds an elongated ultrasonic surgical tool and contains means for exciting longitudinal ultrasonic vibrations in the tool. The vibrating tool when applied to tissue, such as a crystalline lens of the eye which has developed a cataract, is capable of breaking the tissue into small pieces. The tool is provided with a means for supplying an irrigation fluid to the surgical site and an aspiration means for removing the irrigation fluid and fragmented tissue from the surgical site. The aspiration means includes an axial bore through the ultrasonic tool which is connected to a source of suction whereby the tissue fragments are aspirated from the surgical site, together with the irrigation fluid. Because the ultrasonic surgical tool fragments the excised tissue into very small particles, which are removed with the spent irrigation fluid, the incision of the eyeball need be only large enough to insert the tool therein and is substantially smaller than the incision required for removing the lens in one piece. However, since the surgical wound in the eyeball is only large enough to insert the ultrasonic surgical tool and irrigation means, the surgical field is practically entirely enclosed, and controlling the flow therethrough of irrigation fluid and aspiration fluid is very important. In particular, the suction applied to the aspiration means must be limited to a safe value, to avoid the danger of collapsing the eyeball. A blockage or occlusion may occur, for example, when a piece of fragmented tissue which is larger than the axial bore of the surgical tool is drawn against the entrance to that axial bore. When such a blockage occurs in the aspiration line, the negative pressure or suction in the aspiration conduit between the surgical site and the vacuum pump increases. If the blockage is then suddenly released either by the mechanical action of the ultrasonic tool or by the increased value of the suction force, there is a tendency for the fluid within the surgical site to rush suddenly into the aspiration conduit with perhaps disastrous consequences. This is an especially important problem in ocular surgery because the total volume of the fluid in the surgical site is smaller than the volume of fluid in the irrigation and aspiration lines.

Generally, the systems of the above-mentioned patents which utilize vacuum control systems consisting of on/off solenoid valves and relief valves were not capable of sensing a blockage in the aspiration conduit and then rapidly and positively, under the control of the surgeon, equalizing the pressure in the irrigation and aspiration lines for rapid clearing of a blockage. Accordingly, a new fluid control system was developed and it is set forth in application Ser. No. 865,360, which is now abandoned and was replaced by U.S. application Ser. No. 105,978 that issued as U.S. Pat. No. 4,832,685 on May 23, 1989, of S. W. Haines, whose contents are hereby incorporated by reference in their entirety. The fluid control system defined therein for a surgical irrigation/aspirator allows the excess vacuum in the aspiration tubing after a blockage to be controllably and rapidly released by venting to the irrigation line and not to air. This liquid venting or pressure equalization system provides a faster rise time, reduces the chance for mini collapses of the enclosed surgical site (eye) to occur, and further requires only one irrigation bottle and the use of a check valve to prevent reversed irrigation flow towards that bottle when venting.

In the past it has been known to use a vacuum pump to create a vacuum and thereby achieve aspiration, as is disclosed for example in the Storz Microvit Vitrectomy System. Vacuum pumps though are susceptible to fluid contamination and, as such, precautions must be made to minimize contact of the aspirant with the pump such as by the use of hydropholic filters on the pump input (the vacuum side thereof) and/or electronic devices which sense and warn of excessive fluid levels. Accordingly, peristaltic pumps are now preferred because of their lack of contamination, their good controllability, their relatively high suction capability and the ease with which the pump can be stopped without special provision for avoiding back flow. Such peristaltic pump systems are disclosed in the above-mentioned U.S. patent and also in U.S. Pat. No. 4,713,051 issued Dec. 15, 1987 to D. L. Steppe et al., whose contents are hereby incorporated by reference in their entirety. In the last-mentioned system a surgical cassette is disclosed which achieves aspiration by means of cooperating with a rotary peristaltic pump mounted on a cassette mechanism integral to the control unit.

Peristaltic pumps function by sequentially compressing a segment of tubing between a fixed plate and moving plate (linear) or rollers (rotary), and this motion moves a bulbous of fluid or tissue from the operative site. The plates or rollers are so arranged so that at any time at least one is occluding the tubing against the fixed plate. As the moving plate or roller engages the tubing, a transient pressure increase (TPI) is experienced in the tubing which peaks when the moving plate or roller is fully engaged against the tubing and fixed plate. This TPI decreases to the steady state level until the engagement of the next moving roller or plate against the tubing. The frequency of these TPI's is dependent on the speed of the peristaltic pump, and the amplitude and the capacitance of the system.

By replacing the column of air that was between the pump and the eye with liquid venting to make the system more responsive the air column which acted as a shock absorber for the pump was thereby removed. As mentioned above peristaltic pumps by their operation cause a roller to come in contact with tubing which displaces the fluid at both ends of the tubing by compressing the tubing. Since the above-mentioned fluid venting system has no air in the tubing and due to the fact that the liquid will not compress or expand, turbulence in the eye results. In other words, oscillating turbulence in the eye from the pump will be seen when there is no occlusion in the aspiration line since there is nothing restricting the large variance of flow that is transmitted to the eye. (If there is an occlusion in the aspiration line the oscillation will not be seen because there is high resistance in the line or no flow at all in the eye.) This oscillating turbulence in the eye, due to the changing pressure in the eye, causes the iris to flap around (so called "iris flutter") and the posterior capsule to bounce up and down, both of which movements are undesirable. It is therefore an object of this invention to increase the capacitance of the system while retaining the increased fluidic response gained by the new technologies employed in the vacuum control system.

Thus, a need has arisen for an improved irrigation and aspiration system which remedies these problems of prior systems.

OBJECTS AND SUMMARY OF THE INVENTION

Accordingly, it is a primary object of the present invention to provide an improved responsive surgical irrigation and aspiration system for aspirating fluid from a surgical site.

Another object of the present invention is to provide an improved surgical irrigation and aspiration system which uses a peristaltic pump for aspirating fluid from an enclosed surgical site and a highly responsive liquid venting or pressure equalization means wherein this system more particularly reduces or eliminates the incidences of undesirable tissue movement at that site.

The present invention stops these oscillations without using air which stores energy by placing a novel dampening mechanism just before the peristaltic pump in the aspiration flow line coming from the eye. This dampening mechanism includes a membrane diaphragm along one side of a fluid chamber thereof which communicates directly with the aspiration flow line. The membrane absorbs the fluctuations caused by the displacement of fluid by the rollers of the peristaltic pump thereby keeping the flow constant in the eye. A reflux shield of the dampening mechanism limits the outward movement of the diaphragm and a stop shield limits the inward movement of the diaphragm.

Other objects and advantages of the present invention will become apparent to those persons having ordinary skill in the art to which the present invention pertains from the foregoing description taken in conjunction with the accompanying drawings.

DETAILED DESCRIPTION OF THE PREFERRED EMBODIMENTS

Figure 1:
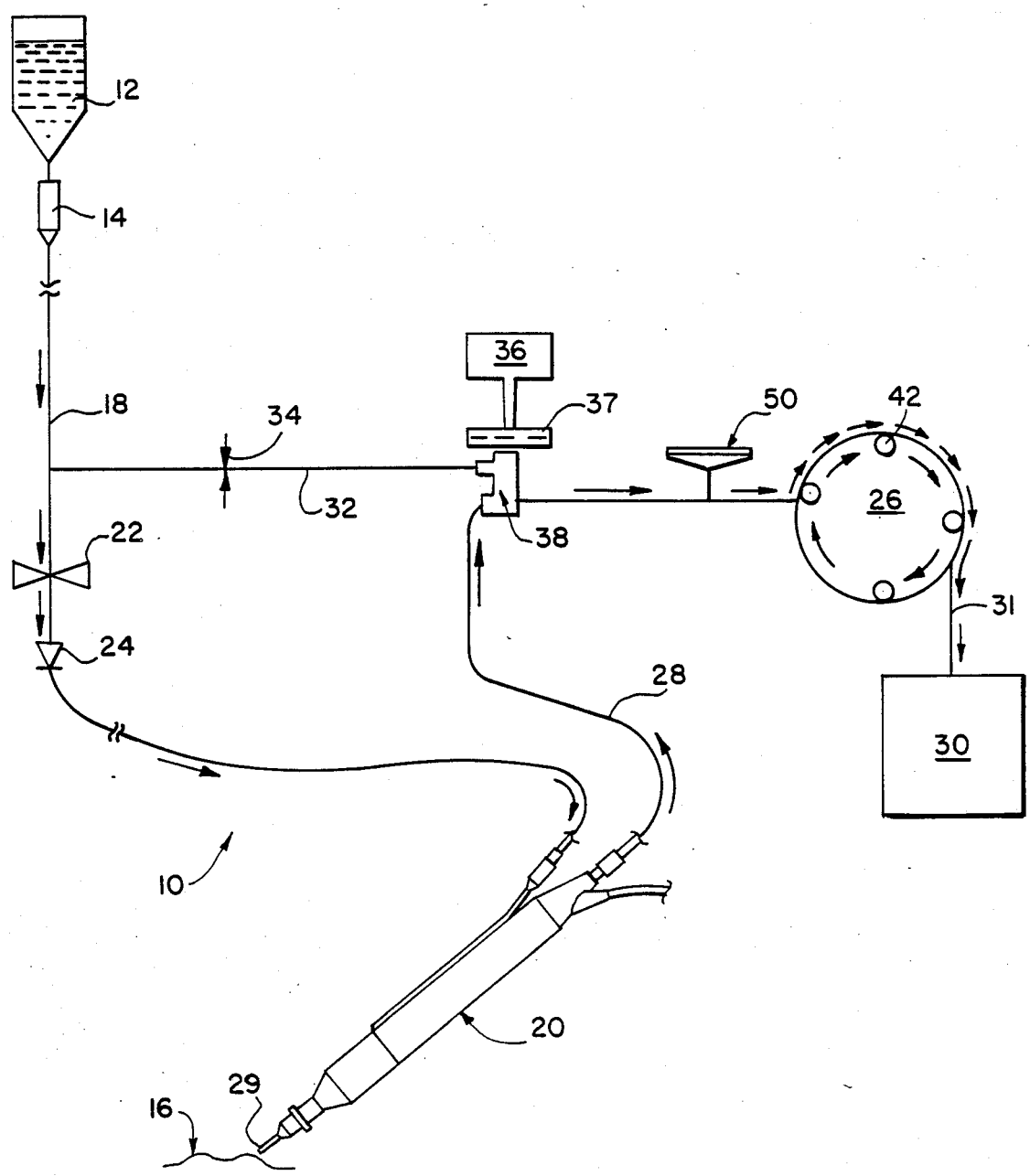
FIG. 1 is a schematic of the fluid circuit of a surgical irrigation and aspiration system of the present invention.

Referring to FIG. 1 a surgical irrigation and aspiration system of the present invention is illustrated schematically generally at 10. System 10 is shown to include a bag or bottle 12 and a drip chamber 14 used to maintain a pressure in the eye shown at 16 and provide BSS for irrigation thereof. The bottle 12 containing BSS is hung on an IV pole which with the drip chamber 14 gives an even gravity flow of irrigation fluid through the irrigation flow line 18 to the handpiece shown generally at 20 and then to the surgical site 16, e.g. eye. An irrigation solenoid or valve 22 is positioned in the irrigation flow line 18 and is used to stop and start the irrigation fluid when needed and is operated by a footswitch controllable by the surgeon. A schematic of an electrical circuit including this footswitch which can be adapted and used to control this fluid flow control system is shown for example in U.S. Pat. 4,832,685 now abandoned and replaced by Ser. No. 105,978. A one-way check valve 24 in the irrigation flow line 18 between the irrigation solenoid 22 and the handpiece 20 prevents the fluid from returning up or back flowing in the irrigation flow line 18 during venting in this liquid system 10 as will be described.

A pump shown generally at 26 and described in greater detail later provides a vacuum to suck aspiration fluid from the surgical site 16 through the handpiece 20 and through the aspiration flow line 28 and then on to a waste material drainage container or bag 30 through drainage line 31. When there is an occlusion in the aspiration flow line 28 such as at the tip 29 of the handpiece 20, a vacuum results in the aspiration flow line 28 as the pump 26 continues to exert a suction force thereto. This vacuum is relieved or vented by the influx of irrigation fluid along the pressure equalization or vent flow line 32 which directly communicates the irrigation flow line 18 and the aspiration flow line 28. The vacuum is thereby quickly relieved by the head pressure of the bottle 12 via the vent solenoid 34. A solid state pressure transducer can be used in place of the solenoid and relief valve 34 in the vent flow line 32 which controls the flow of fluid therethrough.

The valve 34 is normally closed when the handpiece 20 is being used to aspirate fluid and tissue from a surgical site 16. When a blockage occurs in the aspiration flow line 28, such as when a tissue fragment occludes the axial bore in the ultrasonic tool of the handpiece 20, the increased suction in the aspiration flow line 28 is sensed by the pressure sensitive transducer 36 which in turn sends a signal which shuts the pump 26 off. Thereupon, the surgeon can release the vacuum in the aspiration flow line 28 by opening the vent solenoid valve 34 to admit irrigation fluid from the source of irrigation fluid (bottle 12) to the aspiration flow line 28 via the vent flow line 32 and through a special fitting 38 such as is shown and described in detail in U.S. Pat. No. 4,832,685 now abandoned and replaced by Ser. No. 105,978. Since the entire system is filled with liquid, the pressure equalization is very rapid, more rapid than in systems which adjust pressure by admitting air to the system. As soon as the pressure has been equalized, the transducer 36 detects the lower level of suction or vacuum and automatically restarts the pump 26. However, as long as the vent solenoid or valve 34 is open, fluid (irrigation fluid) will flow directly from the source of irrigation fluid or bottle 12 to the aspiration flow line 28 and no substantial amount of suction will be applied to the surgical site 16 through the aspiration flow line. When the valve 34 is closed the pump 26 will again draw fluid from the aspiration flow line 28 and suction will thereby be reapplied to the surgical site. The check valve 24 prevents a backward surge of fluid in the irrigation flow line 18 when the vent valve 34 is open to permit irrigation fluid to flow into the aspiration flow line 28. A filter 37 is provided just before the transducer 36 to prevent bacteria from getting to the transducer.

Figure 2:
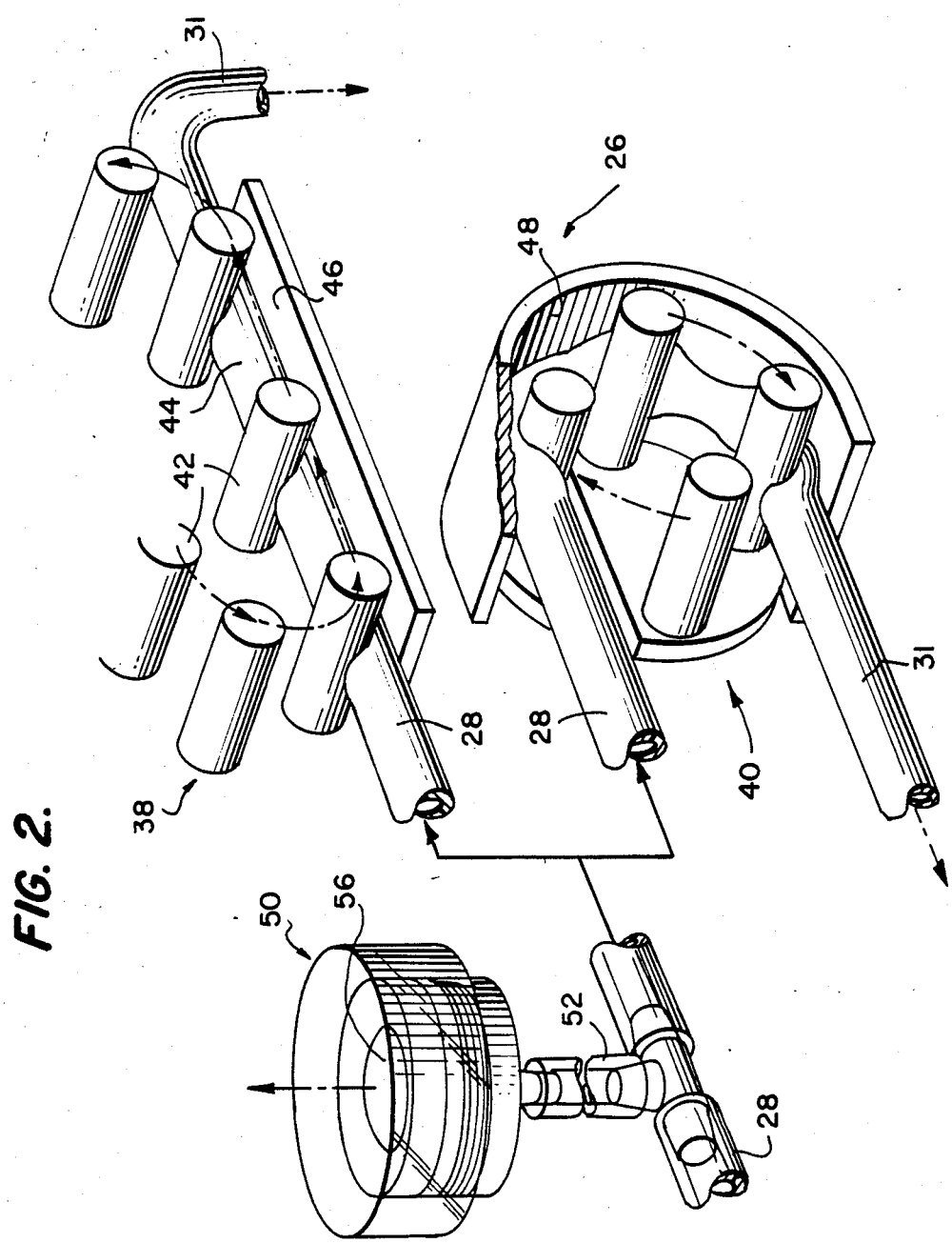
FIG. 2 is a perspective view showing in isolation and in simplified form the oscillation dampening mechanism and alternative peristaltic pump types of the system of FIG. 1 with portions thereof broken away for the sake of clarity.

The pump 26 of the present system is preferably a peristaltic pump, which, referring to FIG. 2, can be either a linear peristaltic pump as shown generally at 38 or a rotary peristaltic pump as shown therebelow generally at 40. The principle of operation of both of these peristaltic pump embodiments is the same in that fluid (aspiration fluid) is pulled in waves by a roller 42 contracting and running along an area of flexible tubing 44. As is apparent from FIG. 2 this area is a generally flat plate 46 for the linear peristaltic pump 38 or a curved plate 48 for the rotary peristaltic pump 40. Examples of peristaltic pumps are disclosed in U.S. Pat. Nos. 4,493,706 and 4,187,057, both of whose entire contents are hereby incorporated by reference.

The action of the rollers 42 on the flexible tubing 44 of the peristaltic pump 26 results in an oscillating turbulence at the surgical site, e.g. the eye, when there is no occlusion in the aspiration flow line 28, causing the iris at the surgical site 16 to flap around and the posterior capsule to bounce up and down. To minimize or substantially stop this undesirable tissue movement, according to the present invention, an oscillation dampening mechanism shown generally at 50 is positioned in the aspiration flow line 28 immediately before the pump 26.

Figure 3:
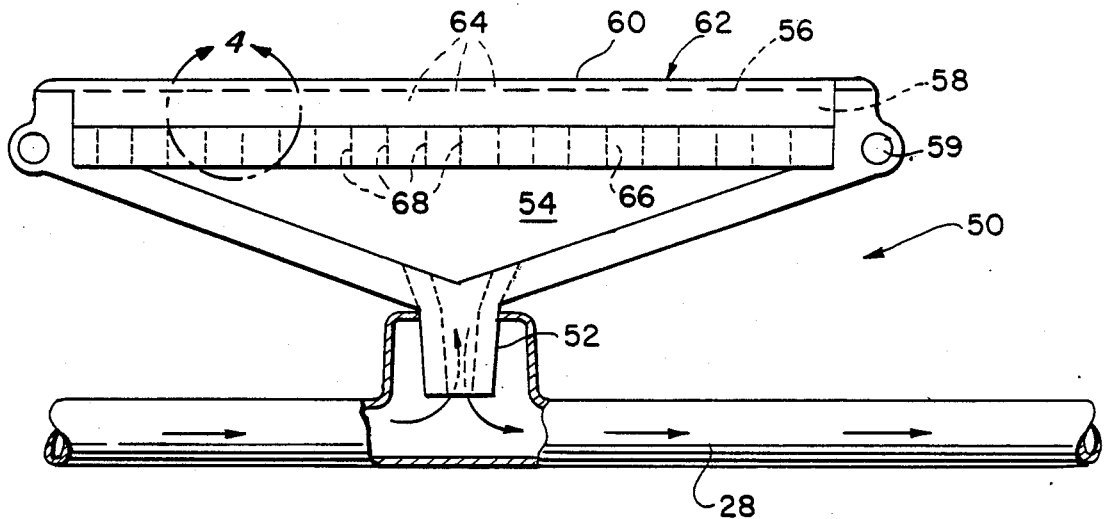
FIG. 3 is a cross-sectional view illustrating in isolation the dampening mechanism of the system of FIG. 1.

The dampening mechanism 50 includes a fluid connector 52, as shown in FIG. 3, providing direct fluid communication with the aspiration flow line 28 to a fluid chamber 54 positioned above it. The fluid chamber 54 is filled with the aspiration fluid and has a rubber flexible diaphragm 56 extending across the top side thereof. A circular support structure 58, including a circular 0-ring 59, is provided to which the diaphragm 56 is attached and stretched across and the structure funnels down to the fluid connector 52 and contains or defines therein the fluid chamber 54. The flexible diaphragm 56 by its flexure movement caused by the oscillating movement of the fluid in the fluid chamber 54 absorbs most if not all of the fluctuations in pressure of the fluid in the fluid chamber 54 and thereby, through the fluid connector 52, dampens the fluid flow oscillations in the aspiration flow line 28 and thus at the surgical site 16.

Figure 4:
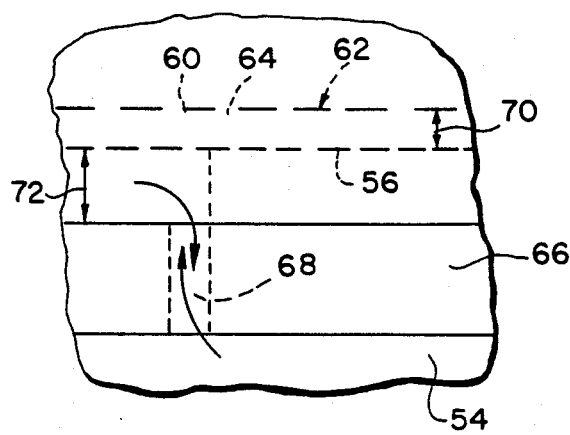
FIG. 4 is an enlarged view of a portion of the dampening mechanism of FIG. 3 taken on line 4 thereof.

A hard cover 60 is positioned spaced outwards from the diaphragm 56 when in its nonflexed position and is supported by the support structure 58. The cover 60 defines a reflux shield shown generally at 62 which limits the diaphragm movement when the reflux is used so that the diaphragm 56 does not expand to too great an extent. A plurality of spaced holes 64 are provided in the hard cover 60 so that a vapor lock after reflux is used does not result. A stop shield 66 is positioned inward of the diaphragm 56 in the fluid chamber 54 and spaced from and generally parallel to the diaphragm when the diaphragm is in its unflexed position. The stop shield 66 limits the movement of the diaphragm 56 so that during an occlusion the diaphragm 56 cannot store energy which would cause a large vacuum when the occlusion is broken. The stop shield 66 similarly has a plurality of passageways or openings 68 passing therethrough to cause it to act as a screen so that the chamber fluid can pass generally freely through it but the inward flexure movement of the diaphragm is limited. The relative positionings and spacings of the stop shield 66 and the reflux shield 62 with respect to the diaphragm 56 are best shown in FIG. 4 where it is seen that the reflux shield 62 is spaced from the diaphragm 56 by a distance denoted by reference numeral 70 and the stop shield 66 on the opposite side by a distance denoted by reference numeral 72.

The dampening mechanism 50 has proven very effective in tests. Using a 5441 Storage Tektronix Oscilloscope with a transducer placed at the tip of the handpiece 20 the pressure changes taking effect in the eye 16 while the pump 26 was running with no occlusion can be precisely seen. In one test conducted it was observed that without the dampening mechanism 50 of the present invention the pressure changes were about twenty millimeters of pressure and with the dampening mechanism in place the pressure changes were reduced to about only one to two millimeters of pressure. Other tests were also conducted with the pump 26 operating at its fastest speed of forty cubic centimeters per minute, and at the normal preferred operating speed of twenty-five cubic centimeters per minute. The reduction of pulsing noted in the eye 16 with the use of the subject dampening mechanism 50 with these last two mentioned tests was similarly by a factor of about ten to twenty times.

From the foregoing detailed description, it will be evident that there are a number of changes, adaptations, and modifications of the present invention which come within the province of those persons skilled in the art. However, it is intended that all such variations not departing from the spirit of the invention be considered as within the scope thereof as limited solely by the claims appended hereto.

What is claimed is:

1. A surgical irrigation and aspiration system for aspirating fluid from a surgical site comprising:

a surgical tool having irrigation and aspiration functions, an irrigation fluid means for providing irrigation fluid to said surgical tool, a peristaltic pumping means for pumping aspiration fluid from the surgical site generally through and away from said surgical tool, an aspiration fluid flow conduit providing a fluid connection between said surgical tool and said peristaltic pumping means for aspiration fluid, a dampening means for dampening the oscillations of the aspiration fluid flow at the surgical site caused at least in part by said peristaltic pumping means, in said aspiration fluid flow conduit, pressure equalization means for equalizing the pressure in said aspiration fluid flow conduit when said tool becomes occluded, wherein said equalization means is a liquid venting means, and said dampening means comprising a fluid connector in fluid communication with said aspiration fluid flow conduit, a fluid chamber fillable with fluid and communicatable through said fluid connector with said aspiration fluid flow conduit so as to increase fluidic capacitance of the system, and a flexible diaphragm extending across at least part of a side of said fluid chamber, said flexible diaphragm by its flexure movement caused by the fluid in said fluid chamber absorbing at least a portion of the fluctuations of the fluid in said fluid chamber and thereby, through said fluid connector, dampening the fluid flow oscillations in said aspiration fluid flow conduit and at the surgical site, said dampening means to prevent oscillating turbulence in the eye and prevent the iris from flutter and the posterior capsule from bouncing during aspiration.

2. The system of claim 1 wherein said fluid connector is disposed in said aspiration fluid flow conduit at a location generally adjacent to said peristaltic pumping means.

3. The system of claim 1 wherein said peristaltic pumping means comprises a rotary peristaltic pump.

4. The system of claim 1 wherein said peristaltic pumping means comprises a linear peristaltic pump.

5. The system of claim 1 wherein said liquid venting means includes a means for irrigation fluid to flow from said irrigation fluid supply means to said aspiration fluid flow conduit.

6. The system of claim 1 wherein said surgical tool includes an ultrasonic fragmenting means, and the aspiration fluid in said aspirator fluid flow conduit includes particles of material fragmented at the surgical site by said ultrasonic fragmenting means.

7. The system of claim 1 wherein said fluid connector is disposed at right angles to said aspiration fluid flow conduit.

8. The system of claim 1 wherein said flexible diaphragm comprises a rubber membrane.

9. The system of claim 1 wherein said dampening means includes an outward means positioned generally outside of said fluid chamber for limiting the outward flexure movement of said flexible diaphragm.

10. The system of claim 9 wherein said outward means comprises a screen fixed in a position spaced outwards a distance from said flexible diaphragm when in its unflexed position.

11. The system of claim 9 wherein said outward means comprises a hard cover fixed in a position spaced outwards a distance from said flexible diaphragm when said flexible diaphragm is in its unflexed position, and said hard cover defining a plurality of openings therethrough.

12. The system of claim 1 wherein said dampening means includes an inward means positioned generally in said fluid chamber for limiting the inward movement of said flexible diaphragm.

13. The system of claim 12 wherein said inward means comprises a stop shield fixed in a position spaced inwards a distance from said flexible diaphragm when said flexible diaphragm is in its unflexed position, and defining a plurality of openings therethrough through which the fluid in said fluid chamber can pass generally freely from one side of said stop shield to the other.

14. The system of claim 12 wherein said dampening means further includes an outward means positioned generally outside of said fluid chamber for limiting the outward flexure movement of said flexible diaphragm.

15. The system of claim 1 wherein said fluid of said fluid chamber is aspiration fluid.

16. The system of claim 1 further comprising a drainage container into which the aspiration fluid in said aspiration fluid flow conduit flows.

17. The system of claim 1 wherein said irrigation fluid means comprises a container of irrigation fluid positioned above the surgical site for gravity drainage thereto, a flow line between said container and said surgical tool, and a check valve means for preventing the flow of irrigation fluid in said flow line towards said container.

18. The system of claim 17 wherein said irrigation fluid means further comprises a solenoid valve in said flow line for controlling the flow of irrigation fluid to said surgical tool.

19. The system of claim 1 wherein said surgical tool is a phacoemulsification handpiece, and the surgical site is a chamber of the eye.

20. For a surgical irrigation and aspiration system for aspirating fluid from a surgical site including a surgical tool having irrigation and aspiration functions, an irrigation fluid means for providing irrigation fluid to the surgical tool, a peristaltic pumping means for pumping aspiration fluid from the surgical site generally through and away from the surgical tool, and an aspiration fluid flow conduit providing a fluid connection between the surgical tool and the peristaltic pumping means, a dampening device for dampening the oscillations of the aspiration fluid flow, caused at least in part by the peristaltic pumping means, in the aspiration fluid flow conduit, comprising:

a fluid connector positionable so as to be in fluid communication with the aspiration fluid flow conduit, a fluid chamber fillable with fluid and communicatable through said fluid connector with the aspiration fluid flow conduit so as to increase fluidic capacitance of the system, a flexible diaphragm extending across at least part of a side of said fluid chamber, and said flexible diaphragm by its flexure movement caused by the fluid in said fluid chamber absorbing at least a portion the fluctuations in pressure of the fluid in said fluid chamber and thereby, through said fluid connector, dampening the fluid flow oscillations in the aspiration fluid flow conduit and at the surgical site, said dampening means to prevent oscillating turbulence in the eye and prevent the iris from flutter and the posterior capsule from bouncing during aspiration.

21. The device of claim 20 wherein said fluid connector is operatively disposable in the aspiration fluid flow conduit at a location generally adjacent to the peristaltic pumping means.

22. The device of claim 20 wherein said fluid connector is operatively disposable at right angles to the aspiration fluid flow conduit.

23. The device of claim 20 wherein said flexible diaphragm comprises a rubber membrane.

24. The device of claim 20 further comprising an outward means positioned generally outside of said fluid chamber for limiting the outward flexure movement of said flexible diaphragm.

25. The device of claim 24 wherein said outward means comprises a screen fixed in a position spaced outwards a distance from said flexible diaphragm when said flexible diaphragm is in its unflexed position.

26. The device of claim 24 wherein said outward means comprises a hard cover fixed in a position spaced outwards a distance from said flexible diaphragm when said flexible diaphragm is in its unflexed position, and said hard cover defining a plurality of openings therethrough.

27. The device of claim 20 further comprising an inward means positioned generally inside of said fluid chamber for limiting the inward movement of said flexible diaphragm.

28. The device of claim 27 wherein said inward means comprises a stop shield fixed in a position spaced inwards a distance from said flexible diaphragm when said flexible diaphragm is in its unflexed position, and defining a plurality of openings therethrough through which the fluid in said fluid chamber can pass freely from one side of said stop shield to the other.

29. The device of claim 27 further comprising an outward means positioned generally outside of said fluid chamber for limiting the outward flexure movement of said flexible diaphragm.

30. The device of claim 20 wherein said fluid chamber is configured as a cone with its tip connected to said fluid connector and said flexible diaphragm covering the larger end thereof opposite said tip.

31. The device of claim 20 wherein said fluid of said fluid chamber is aspiration fluid from the aspiration fluid flow conduit.

32. The device of claim 20 wherein said diaphragm is disposed directly opposite to said fluid connector across said fluid chamber.

33. A surgical irrigation and aspiration system for aspirating fluid from a surgical site comprising:
  a surgical tool having irrigation and aspiration functions,
  an irrigation fluid means for providing irrigation fluid to said surgical tool,
  a peristaltic pumping means for pumping aspiration fluid from the surgical site generally through and away from said surgical tool,
  an aspiration fluid flow conduit providing a fluid connection between said surgical tool and said peristaltic pumping means for aspiration fluid,
  a dampening means for dampening the oscillation of the aspiration fluid flow, caused at least in part by said peristaltic pumping means, in said aspiration fluid flow conduit,
  said dampening means comprising a fluid connector in fluid communication with said aspiration fluid flow conduit, a fluid chamber fillable with fluid and communicatable through said fluid connector with said aspiration fluid flow conduit, and a flexible diaphragm extending across at least part of a side of said fluid chamber, said flexible diaphragm by its flexure movement caused by the fluid in said fluid chamber absorbing at least a portion the fluctuations in pressure of the fluid in said fluid chamber and thereby, through said fluid connector, dampening the fluid flow oscillations in said aspiration fluid flow conduit, and said dampening means to prevent oscillating turbulence in the eye and prevent the iris from flutter and the posterior capsule from bouncing during aspiration.

34. A surgical irrigation and aspiration system for aspirating fluid from a surgical site comprising:
  a surgical tool having irrigation and aspiration functions,
  an irrigation fluid means for providing irrigation fluid to said surgical tool,
  a peristaltic pumping means for pumping aspiration fluid from the surgical site generally through and away from said surgical tool,
  an aspiration fluid flow conduit providing a fluid connection between said surgical tool and said peristaltic pumping means for aspiration fluid,
  a dampening means for dampening the oscillations of the aspiration fluid flow caused at least in part by said peristaltic pumping means, in said aspiration fluid flow conduit, and
  said dampening means comprising a fluid connector in fluid communication with said aspiration fluid flow conduit, a fluid chamber fillable with fluid and communicatable through said fluid connector with said aspiration fluid flow conduit, and a flexible diaphragm extending across at least part of a side of said fluid chamber, said flexible diaphragm by its flexure movement caused by the fluid in said fluid chamber absorbing at least a portion the fluctuations in pressure of the fluid in said fluid chamber and thereby, through said fluid connector, dampening the fluid to prevent oscillating turbulence in the eye and prevent the iris from flutter and the posterior capsule from bouncing during aspiration, and said fluid chamber is configured as a cone with its tip connected to said fluid connector and said flexible diaphragm covers its larger end opposite said tip.

35. For a surgical irrigation and aspiration system for aspirating fluid from a surgical site including a surgical tool having irrigation and aspiration functions, an irrigation fluid means for providing irrigation fluid to the surgical tool, a peristaltic pumping means for pumping aspiration fluid from the surgical site generally through and away from the surgical tool, and an aspiration fluid flow conduit providing a fluid connection between the surgical tool and the peristaltic pumping means, a dampening device for dampening the oscillations of the aspiration fluid flow, caused at least in part by the peristaltic pumping means, in the aspiration fluid flow conduit, comprising:
  a fluid connector positionable so as to be in fluid communication with the aspiration fluid flow conduit,
  a fluid chamber fillable with fluid and communicatable through said fluid connector with the aspiration fluid flow conduit,
  a flexible diaphragm extending across at least part of a side of said fluid chamber, and
  said flexible diaphragm by its flexure movement caused by the fluid in said fluid chamber absorbing at least a portion the fluctuations in pressure of the fluid in said fluid chamber and thereby, through said fluid connector, dampening the fluid flow oscillations in the aspiration fluid flow conduit, and said device to prevent oscillating turbulence in the eye and prevent the iris from flutter and the posterior capsule from bouncing during aspiration at the surgical site by at least about ninety percent.

* * * * *